United States Patent [19]

Czaban et al.

[11] Patent Number: 4,531,088
[45] Date of Patent: Jul. 23, 1985

[54] BLOOD ANALYSIS

[75] Inventors: John D. Czaban, Bradford; Alan D. Cormier, Newburyport; Kenneth D. Legg, Wellesley, all of Mass.

[73] Assignee: Allied Corporation, Morristown, N.J.

[21] Appl. No.: 405,870

[22] Filed: Aug. 6, 1982

[51] Int. Cl.³ .............................................. G01N 27/00
[52] U.S. Cl. .................................. 324/71.1; 324/438; 324/450; 204/411
[58] Field of Search ................. 324/71.1, 425, 450, 324/438; 204/403, 406, 409, 411, 416

[56] References Cited

U.S. PATENT DOCUMENTS

| | | |
|---|---|---|
| 3,398,079 | 8/1968 | Arthur et al. ............... 204/195 |
| 3,505,196 | 4/1970 | Dahms ......................... 324/425 |
| 3,648,159 | 3/1972 | Stansell et al. ............. 324/438 |
| 3,649,504 | 3/1972 | Evans et al. ................. 204/195 |
| 3,658,478 | 4/1972 | Spergel et al. .............. 23/253 |
| 3,732,159 | 5/1973 | Platt ........................... 204/195 |
| 3,840,438 | 10/1974 | Ast et al. ................... 204/1 T |
| 3,853,732 | 12/1974 | Brand et al. ................. 204/195 |
| 3,874,850 | 4/1975 | Sorensen et al. ............. 23/230 |
| 3,894,917 | 7/1975 | Riseman et al. .............. 204/1 T |
| 3,997,420 | 12/1976 | Buzza .......................... 324/450 |
| 4,109,505 | 8/1978 | Clark et al. ................. 73/1 R |
| 4,202,747 | 5/1980 | Buzza et al. ................. 204/411 |
| 4,283,262 | 8/1981 | Cormier et al. .............. 204/411 |

Primary Examiner—Michael J. Tokar
Assistant Examiner—Kevin D. O'Shea
Attorney, Agent, or Firm—Lowell H. McCarter

[57] ABSTRACT

Rapid and accurate whole blood analysis measurements are made with analysis systems of the potentiometric type that employ restricted diffusion type liquid junctions where the whole blood sample is flowed past sensing electrode and liquid junction at a velocity of at least one centimeter per second during a data acquisition interval that is at least twenty-five milliseconds in duration.

14 Claims, 4 Drawing Figures

BLOOD ANALYSIS

This invention relates to analysis systems and more particularly to the potentiometric analysis of liquid samples such as biological fluids.

It is frequently desired to obtain an accurate measurement of one or more constituents of a blood sample of small volume. For example, the values of particular constituents of a blood sample may be useful in providing diagnostic information or in evaluating the effectiveness of therapeutic measures. Potentiometric analysis systems employing electrochemical electrodes have been used for measurements of concentration of ions of hydrogen, sodium, potassium and the like. In such systems, the sample to be analyzed is drawn or injected into an analysis chamber for exposure to an ion selective membrane (of glass or plastic material, for example) of a measuring electrode, the magnitude of the electrical potential developed at the sample-membrane interface being related to the ionic concentration of the constituent of interest in the sample solution being analyzed. Typically this measurement involves the measurement of the sum of a series of potentials: the potential of a reference electrode; the potential of the measuring electrode; and the junction potential that occurs at the interface between the blood sample and an electrolyte salt bridge solution (a typical electrolyte being saturated KCl). In general, such liquid junctions are either of the "open" type in which there is opportunity for hydrodynamic transport (flow) of salt bridge electrolyte across the junction into the sample solution, or of the "restricted diffusion" type in which there is essentially no hydrodynamic transport (mass flow) across the junction. Junctions of the "restricted diffusion" type use materials such as ceramic frit, platinum mesh or dialysis membranes and predominately establish electrical continuity between the electrolyte and the sample solution by ionic diffusion. Most potentiometric analyzer systems for blood and other biological fluids stop the sample during the electrical potential measurement interval to minimize the sample volume requirement, and to eliminate junction noise artifacts due to the flowing sample as well as interference from electrical sources such as pump motors.

Potentiometric analyzer systems with liquid junctions of the "restricted diffusion" type are generally preferred over systems with junctions of the "open" type, as the latter are more expensive to manufacture as complex configuration and channel dimension considerations are frequently involved, require sample transport arrangements that minimize pulsatile flow of the sample, and are more difficult to maintain, due both to the consumption of electrolyte and the frequent cleaning of the "open" junction channels that is necessary because of plugging. Nonetheless, for measurements of whole blood, systems with liquid junctions of the "open" type have had an advantage as they have response times that are faster than heretofore available systems with junctions with the "diffusion" type, due to a requirement of a relatively long equilibration interval (in excess of one minute) for the measuring system in the latter type of systems to stabilize. Also, in analysis systems with diffusion type liquid junctions, a sodium ion bias has been observed between whole blood and its plasma, a bias of about 0.7 millivolts being observed at normal hematocrit (40%) values.

In accordance with the invention, rapid and accurate whole blood analysis measurements are made with analysis systems of the direct potentiometry type that employ liquid junctions of the diffusion type in which the whole blood sample is flowed past the sensing electrode and liquid junction at a velocity of at least one centimeter per second during a data acquisition interval (the interval that electrical potential measurements are taken). Preferably that data acquisition interval has a duration of at least twenty-five milliseconds during which interval the data signals are averaged by suitable means such as digital filtering.

An analyzer of the potentiometric type in accordance with the invention includes means for supplying a sample fluid to be analyzed, structure defining a sample flow path that has an inlet connected to the sample supplying means, an outlet, and an electrode array connected to the sample flow path that includes a reference electrode system with a liquid junction of the restricted diffusion type and a measuring electrode system with an ion-selective surface portion, the liquid junction and ion-selective surface forming portions of the sample flow path. Means are connected to the flow path for flowing a sample to be analyzed from the sample supplying means past the electrode systems and data acquisition means is connected to the measuring and reference electrode systems. The analyzer also includes control means for enabling the data acquisition means to measure the electrical potential across the electrode systems while the flow means is flowing the sample to be analyzed past the electrode systems. Preferably, the data acquisition means includes an averaging circuit and is enabled during an interval of at least twenty-five milliseconds while the sample is being flowed past the electrode systems at a velocity of at least one centimeter per second. The restricted diffusion liquid junction preferably is a dialysis membrane that has a molecular weight cutoff of less than sixty thousand. In a particular embodiment, the system includes measuring electrodes for sensing sodium and potassium, the sodium sensing electrode including a glass membrane and the potassium sensing electrode including a valinomycin membrane, and the dialysis membrane is of cellophane and has a molecular weight cutoff of about two thousand. In that particular embodiment the averaging is accomplished by the charging of a capacitor in a sample and hold circuit, the width of the whole blood analysis conduit is in the order of 0.7 millimeter, the diffusion junction employs a dialysis membrane that is seated against a port that has a width dimension of similar value for exposure to the sample to be analyzed, and the flow rate is such that the transition interval of a whole blood cell across the diffusion junction interface is less than one tenth of a second.

Analyzers in accordance with the invention eliminate the previously observed blood-plasma bias, and the time interval required from data sampling to data display is less than one-half minute as the previously required equilibration interval is not necessary. Flushing and calibration sequences are simplified.

Other features and advantages of the invention will be seen as the following description of a particular embodiment progresses, in conjunction with the drawings, in which.

DESCRIPTION OF PARTICULAR EMBODIMENT

Figure 1:
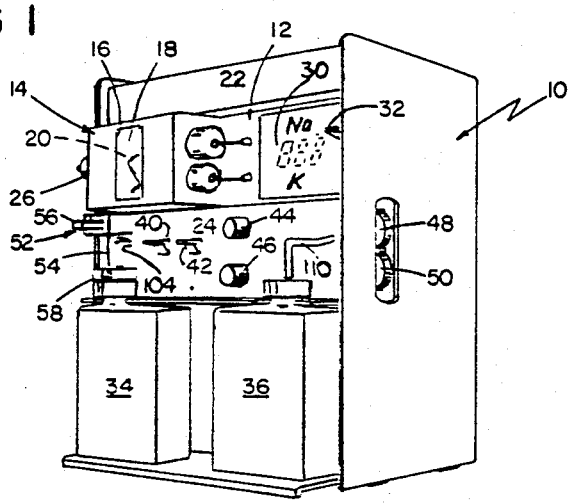
FIG. 1 is a perspective view of analyzer apparatus in accordance with the invention.

The analyzer shown in FIG. 1 includes a housing 10 that has a front surface 12 on which a measuring module 14 is mounted. Module 14 has a front viewing window 16 behind which is mounted a transparent acrylic analysis cell 18 that has a flow through passage 20. Coupled to flow passage 20 are reference electrode 22, potassium electrode 24 and sodium electrode 26. To the right of module 14 is digital display 30 with selector switch 32 for selecting either sodium data or potassium data. Mounted below module 14 is waste bottle 34 and below display 30 is flush reservoir 36. Controls on the housing include aspiration control lever 40, flush control lever 42, sodium balance control 44, potassium balance control 46, sodium slope control 48, and potassium slope control 50. Sample inlet assembly 52 includes probe 54 and handle 56. Probe 54 is supported for pivoting movement between a vertical (rest) position in which flow from the probe 54 is directed through the cap 58 into waste bottle 34 and an inclined position in which the probe tip is exposed for insertion into a sample container.

Figure 2:
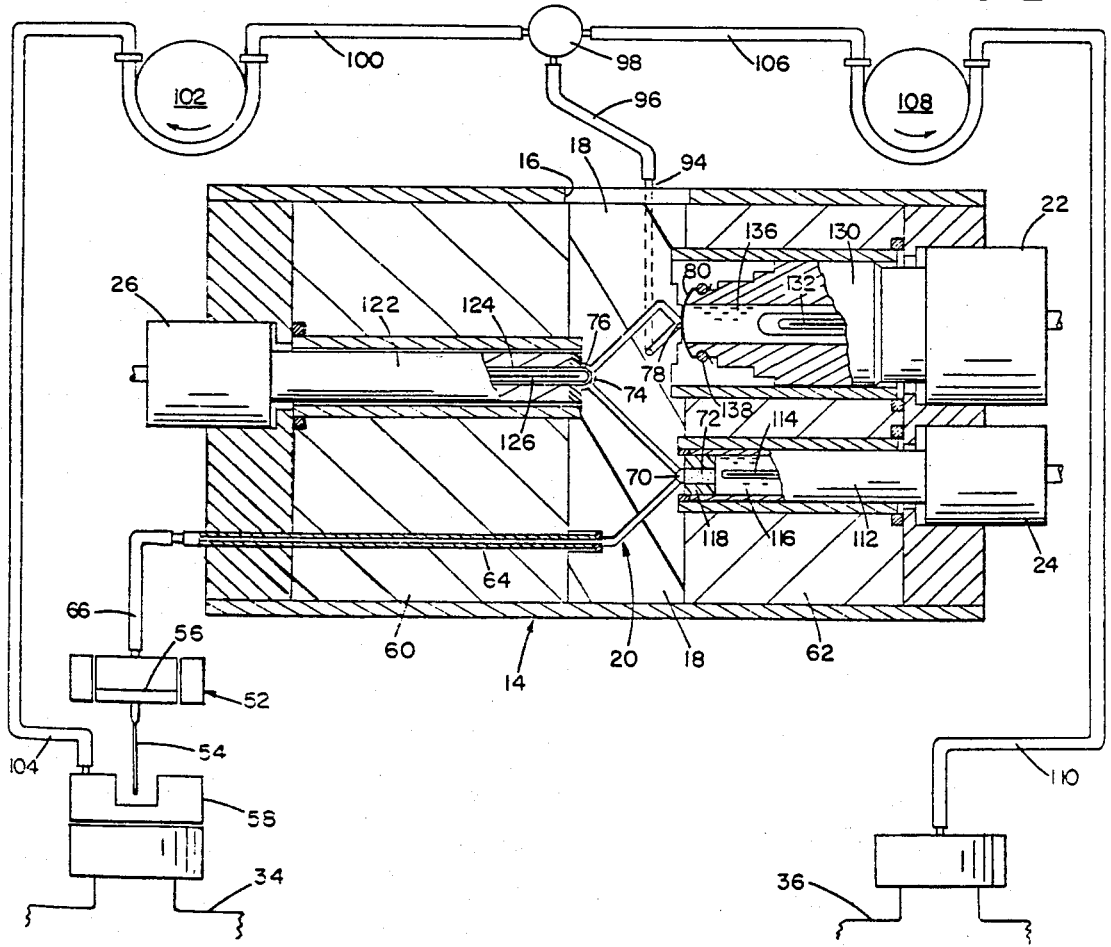
FIG. 2 is a sectional view of the sensor-flow path module of the analyzer of FIG. 1 showing the electrode configurations and associated fluid flow paths.

Further details of the system may be seen with reference to FIG. 2—a sectional view of the sample flow path 20, the electrodes 22, 24, 26, and associated flow tubes and pumps. Module 14 includes acrylic block 18 through which the sample flow path 20 is drilled and aluminum blocks 60, 62 which house the electrodes 22, 24, 26 and provide thermal stability. Inlet tube 64 is connected to aspirator probe 54 by tubing 66. The sample to be analyzed is flowed through inlet tube 64 into serpentine flow path 20 in measuring cell 18 that extends to sensing port 70 against which the tip 72 of potassium electrode 24 is seated; to cavity 74 that receives the tip 76 of sodium sensing electrode 26; and to port 78 against which the dialysis membrane 80 of reference electrode 22 is seated. From port 78, the serpentine flow path extends to the outlet 94 of the flow through cell 18. Connected to outlet 94 by tubing 96 is Tee 98. Path 100 extends through peristalic pump 102 and tube 104 to cap 58 of waste bottle 34, and path 106 extends through peristalic pump 108 and tube 110 to flush bottle 36.

Potassium electrode 24 includes a main body 112 with reference electrode 114 and an electrolyte solution chamber 116 with a tygon ring 118 at its tip that carries a valinomycin membrane 72. Sodium electrode 26 has a housing 122 with a glass tube 124 that contains an electrolyte solution and a electrode wire 126. The tip 76 of tube 124 is made of sodium sensitive glass and projects into sensing cavity 74. Reference electrode 22 has body 130 that carries a calomel electrode 132 housed in glass tube 134 which has lateral orifices that make contact with potassium chloride electrolyte solution in compartment 136. A cellophane dialysis membrane 80 (about 2.6 mils in thickness and with a molecular weight cutoff of about 2000), secured by O-ring 138 on the tip of electrode 22, allows ionic diffusion, thus providing electrical continuity between the electrodes, while preventing the KCL electrolyte solution from mixing with the sample in the flow path 20.

Figure 3:
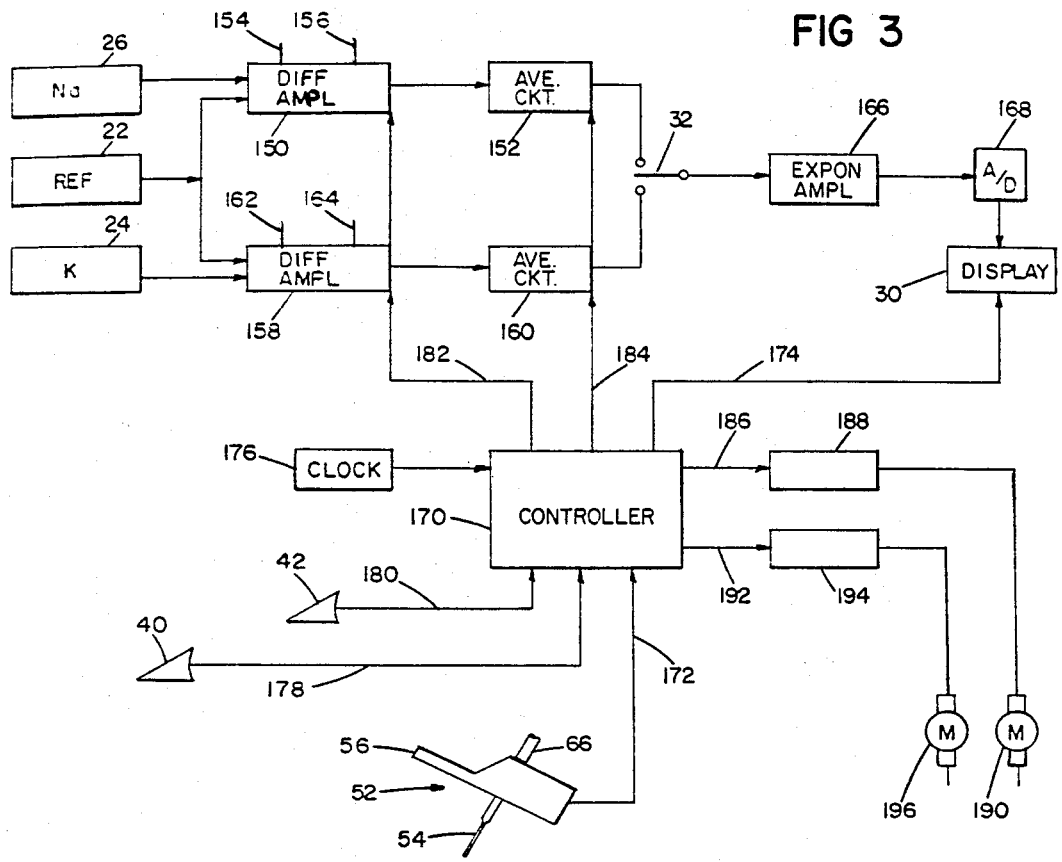
FIG. 3 is a block diagram of control arrangements of the analyzer of FIG. 1.

The block diagram of FIG. 3 shows the sodium electrode 26 and the reference electrode 22 connected to differential amplifier stage 150 and averaging stage 152 (a sample and hold circuit). Signals from the sodium and reference electrodes are applied to stage 150, and signals from slope and balance controls are applied to inputs 154, 156. The similar circuitry associated with the potassium electrode 24 includes differential amplifier stage 158 and averaging stage 160 (also a sample and hold circuit). Signals from the potassium and reference electrodes 24, 22 are applied to stage 158, and signals from slope and balance controls are applied to inputs 162, 164. The display selector 32 channels the signal from the selected sample and hold circuit 152, 160 through an exponential amplifier 166 to an analog-to-digital converter 168 for application to display 30. (When the aspiration tip 54 is in its "up" position, a signal is generated over line 172 to controller 170 which generates a signal on line 174 to blank out the LED display 30.) A master clock 176 and controller 170 determine the duration of the aspiration and flush cycles which are initiated respectively by sample lever 40 (a signal over line 178) and by flush lever 42 (a signal over line 180). When the aspirator probe 54 is raised, the flush cycle mode is inhibited. Controller outputs are applied to the input stages 150, 158 over line 182, to the sample and hold circuits 152, 160 over line 184, to the display 30 over line 174, over line 186 via drive circuit 188 to motor 190 of aspirate pump 102, and over line 192 to drive flush pump motor 196 via drive circuit 194. The aspiration pump 102 is driven at twelve RPM and the flush pump 108 is driven at 150 RPM.

Figure 4:
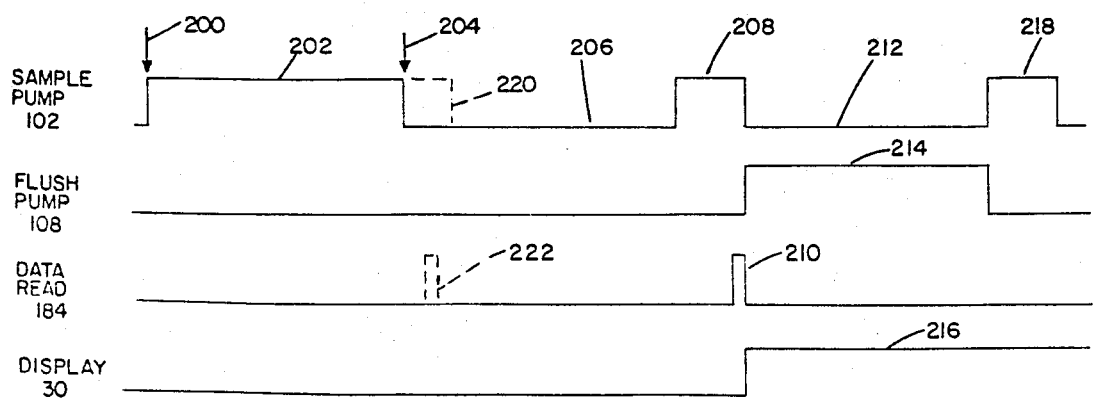
FIG. 4 is a timing diagram illustrating aspects of the operation of analyzers in accordance with the invention.

In analyzer operation, when the handle 56 of the aspirator probe assembly 52 is raised, the display 30 is blanked, and the flush cycle mode is inhibited. After the operator inserts the sample probe 54 in a sample cup, controller 170, in response to depression of aspirator control lever 40 (indicated at 200 in FIG. 4), energizes motor 190 to operate aspirator pump 102 for eleven seconds as indicated at interval 202 in FIG. 4. Sample is flowed from the sample cup through tube 66 and inlet 64 into flow path 20 and past the three electrodes 22, 24, 26 at a velocity of about 2.5 centimeters per second. At the end of the eleven second aspiration interval, the leading edge of the aspirated sample is located in flow path 20 between port 78 and outlet 94. Following the eleven second aspiration interval, the operator removes the sample cup from probe 54 and returns the probe to its vertical position, which generates a signal on line 172 as indicated at 204 in FIG. 4. In response to signal 204, following a twelve second delay interval for sample fluid equilibration as indicated at 206, controller 170 again energizes aspirator pump 102 for a flow interval 208 of three seconds, during which the sample to be analyzed is flowed past the electrodes 22, 24, and 26 at a rate of about 2.5 centimeters per second. In the last one-half second of flow interval 208, the sample and hold circuits 152, 160 are actuated by a signal on line 184 as indicated at 210 and during that one-half second interval, those circuits average the data signals that are generated by the sodium and potassium stages 150, 158 while the sample is being flowed past the electrodes. At the end of that interval, controller 170 deenergizes the sample pump 102 (as indicated at 212) and energizes the flush pump 108 (as indicated at 214) and enables the display 30 by a signal on line 174 as indicated at 216 in FIG. 4. Air segmented flush solution is pumped by flush pump 108 (motor 196) from bottle 36 through the upper port 94 of the flow path module 18 for flow in reverse direction down the sample flow path 20 to the sample probe 54 and expulsion together with any sample residue into waste container 34. The flush solution pumping interval 214 continues for eleven seconds. At the end of the eleven second flush pumping interval, pump 108 is de-energized and sample pump 102 is again energized for a three second interval as indicated at 218 to aspirate flush solution up the sample probe 54 to create an air lock between the flush and the next sample, to eliminate the possibility of a drop of flush solution at the tip of probe 54, and to flow flush solution into tube 100 between Tee 98 and pump 102.

Under the above described flowing conditions the bias between plasma/serum data and its own whole blood data (at hematocrits of 80% or less) is less than two millimoles per liter for sodium.

Where other sample flow path configurations (such as a straight through flow path) are used, the equilibration interval 206 may be omitted, the initial sample flow interval past the electrodes being extended (as indicated at 220) with the data acquisition interval occuring earlier in the analysis cycle as at point 222. Controller 170 then generates the flush and aspiration intervals 214 and 218 immediately after the data acquisition interval 222.

In addition, controller 170 automatically generates a flush sequence every one hundred eighty seconds (the flush sequence including intervals 214 and 218) unless a measurement is in progress, in which case, the flush cycle is initiated one hundred eighty seconds after the tip of probe 54 has been repositioned in alignment with waste bottle 34.

Controller 170 holds the data from each analysis at the display 30 until the next flush cycle is initiated or until an aspiration cycle is initiated by depression of aspirate control lever 40.

In a calibration sequence "Cal 1" is sampled and the differential amplifier controls 44 and 46 are adjusted. The "Cal 2" solution is then sampled and the differential amplifier controls 48 and 50 are adjusted.

While particular embodiments of the invention have been shown and described, various modifications will be apparent to those skilled in the art, and therefore it is not intended that the invention be limited to the disclosed embodiments or to details thereof, and departures may be made therefrom within the spirit and scope of the invention.

What is claimed is:

1. An analysis system of the potentiometric type comprising
   means for supplying a sample fluid to be analyzed,
   structure defining a sample flow path that has an inlet at one end and an outlet at its other end, the inlet of said sample flow path being connected to said sample supplying means,
   an electrode array connected to said sample flow path, said electrode array including a reference electrode system that has a liquid junction of the restricted diffusion type and a measuring electrode system that has an ion-selective surface portion for measuring the concentration of a constituent of interest in the sample fluid to be analyzed, liquid junction and said ion-selective surface portion defining in part said sample flow path,
   flow means connected to said flow path for flowing the sample to be analyzed from said sample supplying means past said electrode systems, and
   data acquisition means, and control means for enabling said data acquisition means to sense the electrical potential across said electrode systems to acquire data on the concentration of a constituent of interest in the sample while said flow means is flowing said sample past said series of electrode systems.

2. The system of claim 1 wherein said data acquisition means includes an averaging circuit, said control means enables said averaging circuit for an interval of at least twenty-five milliseconds while the sample is being flowed past said electrode systems by said flow means, and said acquisition means is enabled during an interval while said flow means is flowing said sample past said section of electrode systems at a velocity of at least one centimeter per second.

3. The system of claim 1 wherein said electrode array includes a plurality of measuring electrodes for sensing sodium and potassium, one of said measuring electrodes including a glass membrane and another of said measuring electrodes including a membrane of plastic material.

4. The system of claim 1 wherein said reference electrode system includes a membrane which defines said diffusion type junction.

5. The system of claim 4 wherein said membrane has a molecular weight cutoff of less than sixty thousand.

6. The system of claim 5 wherein the width of said flow through path is in the order of one millimeter, said diffusion junction employs a dialysis membrane that is seated against a port in said flow path defining structure, said port having a length in the direction of flow in the order of one millimeter, said flow means flows said sample past said port at a flow rate such that the transition interval of a whole blood cell across said diffusion junction interface is less than one tenth of a second said data acquisition means includes an averaging circuit and said control means enables said averaging circuit for an interval of at least twenty-five milliseconds while the sample is being flowed past said electrode systems by said flow means.

7. An analysis system of the potentiometric type comprising
   means for supplying a sample fluid to be analyzed, structure defining a sample flow path that has an inlet at one end and an outlet at its other end, the inlet of said sample flow path being connected to said sample supplying means,
   an electrode array connected to said sample flow path, said electrode array including a reference electrode system that has a liquid junction of the restricted diffusion type and a measuring electrode system that has an ion-selective surface portion for measuring the concentration of a constituent of interest in the sample fluid to be analyzed, said liquid junction and said ion-selective surface portion defining in part said sample flow path,
   flow means connected to said flow path for flowing the sample to be analyzed from said sample supplying means past said electrode systems, and
   data acquisition means including an averaging circuit, and control means for enabling said data acquisition means to sense the electrical potential across said electrode systems and to enable said averaging circuit for an interval of at least twenty-five milliseconds while the sample is being flowed past said electrode systems by said flow means to acquire data on the concentration of a constituent of interest in the sample.

8. The system of claim 7 wherein said averaging circuit includes a sample and hold circuit, and said averaging is accomplished by the charging of a capacitor in said sample and hold circuit.

9. The system of either claim 1 or 7 and further including a supply of calibrating fluid connected to said outlet of said flow path, and second flow means for flowing calibrating fluid from said supply through said flow path to said inlet, and wherein said control means operates said second flow means immediately after said data acquisition interval.

10. A method of potentiometric analysis of a whole blood sample for a constituent of interest that utilizes a reference electrode with a diffusion type liquid junction and a sensing electrode that has an ion-selective surface portion, said reference electrode liquid junction and said ion-selection surface portion of said sensing electrode defining, in part, a sample flow path, comprising the steps of:

flowing said whole blood sample to be analyzed along said flow path to contact said reference electrode liquid junction and said ion-selective surface portion of said sensing electrode at a velocity of at least one centimeter per second; and measuring the electrical potential across said electrodes for analysis of said whole blood sample while flowing said blood sample at said velocity.

11. The method of claim 10 wherein said electrical potential is measured for an interval of at least twenty-five milliseconds while said whole blood sample is being flowed at said velocity past said reference electrode liquid junction and said ion-selective surface portion of said sensing electrode.

12. The method of claim 11 and further including the step of flushing said flow path immediately following said measuring interval.

13. A method of potentiometric analysis of a whole blood sample for a constituent of interest that utilizes a reference electrode with a diffusion type liquid junction and a sensing electrode that has an ion-selective surface portion, said reference electrode liquid junction and said ion-selection surface portion of said sensing electrode defining, in part, a sample flow path, comprising the steps of:

flowing said whole blood sample to be analyzed along said flow path to contact said reference electrode liquid junction and said ion-selective surface portion of said sensing electrode at a velocity of at least one centimeter per second;

measuring the electrical potential across said electrodes for analysis of said whole blood sample while flowing said blood sample at said velocity and averaging said electrical potential during said measuring interval.

14. The method of claim 13 and further including the step of flushing said flow path with a calibrating solution immediately following said measuring interval.

* * * * *

UNITED STATES PATENT AND TRADEMARK OFFICE
CERTIFICATE OF CORRECTION

PATENT NO. : 4,531,088

DATED : July 23, 1985

INVENTOR(S) : John D. Czaban et al

It is certified that error appears in the above-identified patent and that said Letters Patent are hereby corrected as shown below:

Column 6, Claim 2, Line 18, "section" should be "series"

Signed and Sealed this

Twelfth Day of November 1985

[SEAL]

Attest:

Attesting Officer

DONALD J. QUIGG

Commissioner of Patents and Trademarks